(12) United States Patent
Tsubota et al.

(10) Patent No.: US 9,307,949 B2
(45) Date of Patent: Apr. 12, 2016

(54) X-RAY CT DEVICE AND METHOD FOR CORRECTING SCATTERED X-RAYS

(71) Applicant: HITACHI MEDICAL CORPORATION, Chiyoda-ku, Tokyo (JP)

(72) Inventors: Yushi Tsubota, Tokyo (JP); Fumito Watanabe, Tokyo (JP); Hironori Ueki; Yasutaka Konno, Tokyo (JP); Shinichi Kojima, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 147 days.

(21) Appl. No.: 14/364,278

(22) PCT Filed: Dec. 12, 2012

(86) PCT No.: PCT/JP2012/082251
§ 371 (c)(1),
(2) Date: Jun. 10, 2014

(87) PCT Pub. No.: WO2013/089155
PCT Pub. Date: Jun. 20, 2013

(65) Prior Publication Data
US 2014/0328452 A1 Nov. 6, 2014

(30) Foreign Application Priority Data
Dec. 12, 2011 (JP) .................... 2011-270845

(51) Int. Cl.
*A61B 6/00* (2006.01)
*A61B 6/03* (2006.01)
(Continued)

(52) U.S. Cl.
CPC .............. *A61B 6/5282* (2013.01); *A61B 6/032* (2013.01); *G01N 23/046* (2013.01);
(Continued)

(58) Field of Classification Search
CPC ........ A61B 6/032; A61B 6/5282; A61B 6/583; A61B 6/4291; A61B 6/5205; G06T 11/005; G06T 2211/416; G01N 23/046
USPC .................................. 378/4–20; 382/128–131
See application file for complete search history.

(56) References Cited

U.S. PATENT DOCUMENTS 5,905,809 A 5/1999 Timmer
2005/0220357 A1 10/2005 Rifu
(Continued)

FOREIGN PATENT DOCUMENTS

CN 101987021 A 3/2011
JP 05-060930 A 3/1993
(Continued)

OTHER PUBLICATIONS

Chinese Office Action received in corresponding Chinese Application No. 201280060843.X dated Oct. 10, 2015.
(Continued)

*Primary Examiner* — Courtney Thomas
(74) *Attorney, Agent, or Firm* — Mattingly & Malur, PC

(57) ABSTRACT

It is an object to prevent a poor X-ray CT image due to scattered X-rays. An X-ray CT scanner (100) uses an X-ray detector (4), etc., to scan (F1) an object (3) to obtain X-ray transmission image data, and estimate (F3) an X-ray absorption coefficient distribution inside the object (3) based on the scanned X-ray transmission image data. Next, the X-ray CT scanner (100) performs a Monte Carlo simulation on a simulated object (3) having the X-ray absorption coefficient distribution estimated, and estimates (F4 and F7) a point spread function or scattered X-ray distribution derived from the object. Then, the X-ray CT scanner (100) corrects (F5 and F8), based on the point spread function or scattered X-ray distribution estimated, the X-ray transmission image data, and finally creates (F6 and F9) an image of the X-ray absorption coefficient distribution of the object (3).

11 Claims, 7 Drawing Sheets

(51) Int. Cl.
   *G01N 23/04* (2006.01)
   *G06T 11/00* (2006.01)
(52) U.S. Cl.
   CPC ............ *G06T 11/005* (2013.01); *A61B 6/4291* (2013.01); *A61B 6/5205* (2013.01); *A61B 6/583* (2013.01); *G06T 2211/416* (2013.01)

(56) References Cited

U.S. PATENT DOCUMENTS

| 2009/0092222 A1 | 4/2009 | Okamoto et al. | |
|---|---|---|---|
| 2012/0148156 A1* | 6/2012 | Sehnert | A61B 6/4291 382/171 |

FOREIGN PATENT DOCUMENTS

| JP | 07-184886 A | 7/1995 |
|---|---|---|
| JP | 11-299768 A | 11/1999 |
| JP | 3566762 B2 | 6/2004 |
| JP | 2005-058760 A | 3/2005 |
| JP | 4218908 A | 11/2008 |
| JP | 2009-082615 A | 4/2009 |
| JP | 2009-223336 A | 10/2009 |

OTHER PUBLICATIONS

G. Jarry, "Characterization of scattered radiation in kV CBCT images using Monte Carlo simulations", Medical Physics, 2006, pp. 4320-4329, vol. 33, Issue 11.

J. A. Seibert, "X-ray scatter removal by deconvolution", Medical Physics, 1988, pp. 567-575, vol. 15, Issue 4.

T. Sato, "X-sen Kyushu Katei ni Okeru Ryoshi Yuragi no Denpa (Gazo Kogaku Noise Tokusei)", Japanese Journal of Radiological Technology, Aug. 1, 1994, p. 1022, vol. 50, No. 8.

* cited by examiner

FIG.7B
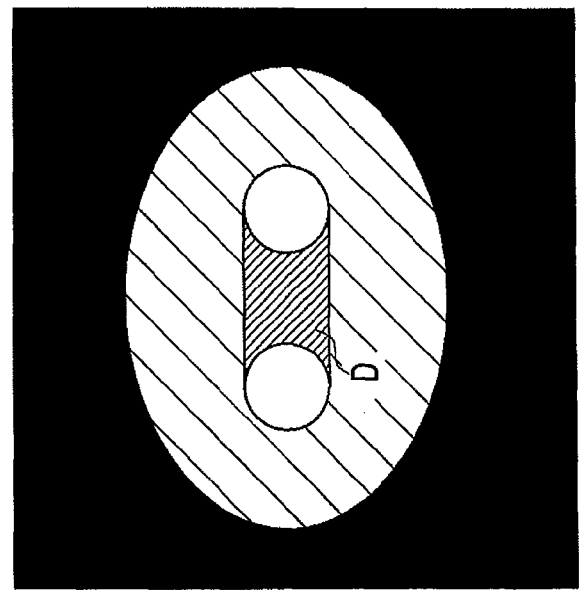
FIG.7A
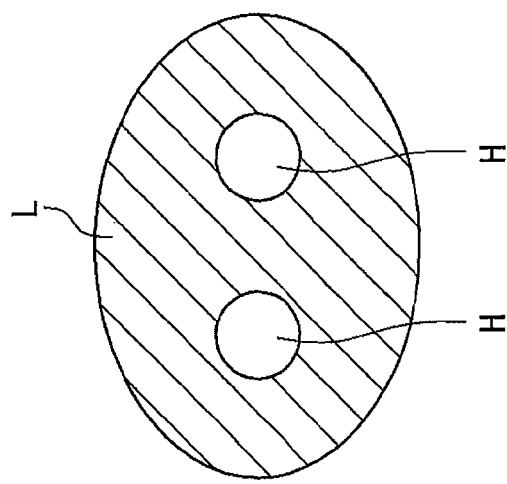

X-RAY CT DEVICE AND METHOD FOR CORRECTING SCATTERED X-RAYS

TECHNICAL FIELD

The present invention relates to an X-ray CT device (or scanner) and a method for correcting scattered X-rays on the data scanned by the X-ray CT device or the like.

BACKGROUND ART

An X-ray CT (Computed Tomography) scanner is a device for reconstructing an image by using a system for processing data having a difference in an X-ray attenuation rate (X-ray absorption coefficient) inside an object. The X-ray CT scanner includes an X-ray source that irradiates an object with X-rays and an X-ray detector that detects X-rays transmitted through the object. The object is interposed between the X-ray source and the X-ray detector, and they face each other. They rotate around the object while keeping a position in which the object is interposed therebetween and they face each other. Then, X-ray transmission image data of the object is scanned from a plurality of projection directions. Usually, it is possible for the X-ray source of the X-ray CT scanner to use an X-ray tube in which an anode is irradiated with electrons accelerated using a high voltage to emit X-rays. In addition, the X-ray detector has a structure having X-ray detection elements arranged like a two-dimensional array so as to quickly scan a broad area at one scan.

Projection data as obtained by a scan using the X-ray CT scanner include not only information on the intensity of X-rays (primary X-rays) transmitted through the object without scattering, but also information on the incident intensity of X-rays (scattered X-rays) scattered in the object, etc. In order to remove the scattered X-rays, the X-ray CT scanner has an anti-scatter grid to remove the scatted X-ray generated in the object and the grid is positioned at the X-ray source side of the X-ray detector. Even this method, however, cannot remove all the scattered X-rays. Because of this, certain software is also used to perform scatter correction (e.g., see the following Patent Literatures 1 to 3).

CITATION LIST

Patent Literatures

Patent Literature 1: JP4218908B
Patent Literature 2: JP2009-82615A
Patent Literature 3: JP3566762B

SUMMARY OF INVENTION

Technical Problem

Recently, X-ray CT devices (or scanners) have increasingly had a multi-slice X-ray detector, thereby making it possible to scan a broad area of an object at one scan. Meanwhile, emergence of the multi-slice X-ray detector allows for a wide X-ray irradiation area of an object. This causes an increase in an amount of scattered X-rays. Accordingly, the increase helps create artifacts on a reconstruction image, which results in poor image quality. When an area having an X-ray high-density absorber such as a bone is scanned, in particular, a ratio of a scattered X-ray-derived detection signal to a primary X-ray-derived detection signal relatively increases. Consequently, an X-ray absorption coefficient of the object may be underestimated.

FIG. 7 schematically illustrates artifacts generated in a reconstruction image. FIG. 7A shows a simulated human body (hereinafter, referred to as a phantom) in which two high-density absorber rods H are present in the inside of a low-density absorber L. When this phantom is scanned, dark band artifacts D, which have a smaller CT number than in an actual situation, are observed between the two high-density absorber rods H as shown in the reconstitution image of FIG. 7B. Note that in FIG. 7, levels of the CT number are represented by an interval (density) of the hatching. Specifically, as the CT number decreases, the interval of the hatching decreases (becomes denser).

Here, it is an object of the present invention to provide an X-ray CT device (or scanner) and a method for scatter correction capable of preventing poor image quality due to scattered X-rays by precisely estimating and correcting the scattered X-rays.

Solution to Problem

In order to solve the above problems, an aspect of the present invention provides an X-ray CT device (or scanner) including: a scanning section that scans an object to obtain X-ray transmission image data of the object from a plurality of projection directions, the scanning section including an X-ray source generating X-rays from an X-ray focus and an X-ray detector having X-ray detection elements in a two-dimensional array so as to detect the X-rays, wherein the X-ray source and the X-ray detector rotate around the object while facing each other and the object is interposed therebetween; an internal-distribution-estimating section that estimates an X-ray absorption coefficient distribution inside the object, based on the X-ray transmission image data scanned by the scanning section; a point-spread-function-estimating section that estimates a point spread function of a scatter derived from the object by performing a Monte Carlo simulation to simulate a physical interaction of the X-rays in a simulated object having the X-ray absorption coefficient distribution estimated by the internal-distribution-estimating section; a correction section that corrects the X-ray transmission image data by processing the point spread function estimated by the point-spread-function-estimating section and the X-ray transmission image date according to a deconvolution integral method; and an image-creating section that creates an image of the X-ray absorption coefficient distribution of the object by using the X-ray transmission image data corrected by the correction section.

Another aspect of the present invention provides an X-ray CT scanner including a scanning section that scans an object to obtain X-ray transmission image data of the object from a plurality of projection directions, the scanning section including an X-ray source generating X-rays from an X-ray focus and an X-ray detector having X-ray detection elements in a two-dimensional array so as to detect the X-rays, wherein the X-ray source and the X-ray detector rotate around the object while facing each other and the object is interposed therebetween; an internal-distribution-estimating section that estimates an X-ray absorption coefficient distribution inside the object, based on the X-ray transmission image data scanned by the scanning section; an X-ray-distribution-estimating section that estimates a distribution of scattered X rays derived from the object by performing a Monte Carlo simulation to simulate a physical interaction of the X-rays in a simulated object having the X-ray absorption coefficient distribution estimated by the internal-distribution-estimating section; a correction section that removes components of the scattered X-rays from the X-ray transmission image data, based on the distribution estimated by the X-ray-distribution-estimating section; an image-creating section that creates an image of the X-ray absorption coefficient distribution of the object by using the X-ray transmission image data in which the components of the scattered X-rays have been removed by the correction section.

Advantageous Effects of Invention

The present invention can provide an X-ray CT scanner and a method for scatter correction capable of preventing poor image quality due to scattered X-rays by precisely estimating and correcting the scattered X-rays.

BRIEF DESCRIPTION OF DRAWINGS

FIG. 7 schematically illustrates artifacts generated in a reconstruction image.

DESCRIPTION OF EMBODIMENTS

The following details embodiments of the present invention (hereinafter, referred to as an "embodiment") by referring to appropriate drawings. Note that parts shared among the respective figures have the same reference signs so as to avoid redundant description.

Figure 1:
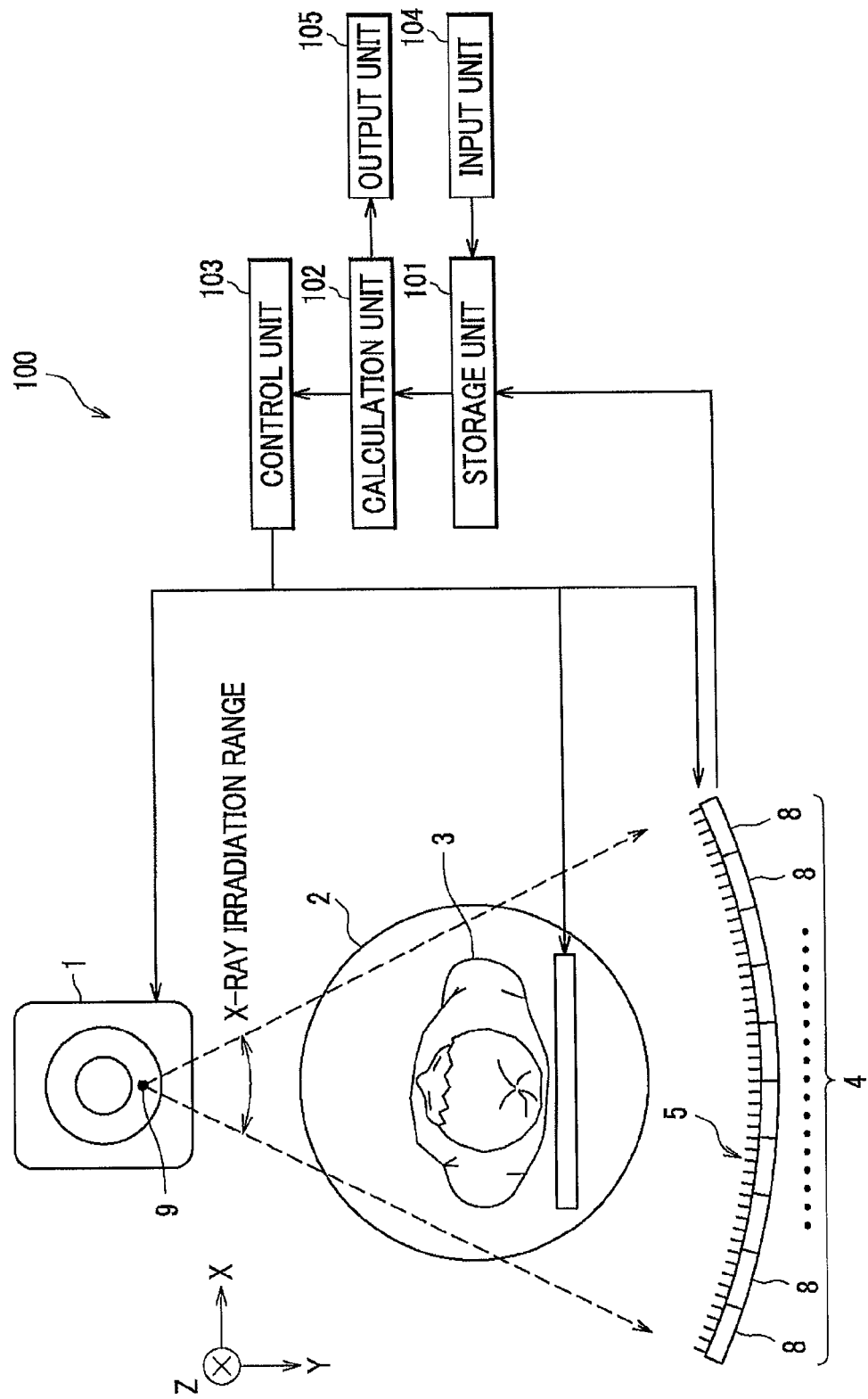
FIG. 1 illustrates how to configure an X-ray CT scanner according to the first embodiment.

<<First Embodiment>>
<Configuration of X-ray CT Scanner 100>
FIG. 1 illustrates how to configure an X-ray CT scanner 100 according to the first embodiment. In the following description, the X-axis direction in FIG. 1 is a channel direction, the Y-axis direction is an X-ray focus direction, and the Z-axis direction is a slice direction. FIG. 1 depicts the X-ray CT scanner 100 viewed from the body axis direction (i.e., the slice direction, the Z-axis direction) of an object 3.

The center portion of a gantry (not shown) of the X-ray CT scanner 100 includes an aperture 2 that allows for entry of the object 3. In addition, a scanner device of the X-ray CT scanner 100 includes an X-ray tube 1 as an X-ray source and an X-ray detector 4. These parts are rotatively supported by the gantry and rotate around the aperture 2 using its center as a rotation axis. Such a configuration enables the object 3 in the aperture 2 to be scanned while the parts rotate.

The X-ray tube 1 as an X-ray source emits X-rays from an X-ray focus 9 which has a limited size in the X-ray tube 1. The X-ray detector 4 is positioned facing the X-ray tube 1, and the object 3 is interposed therebetween. The X-ray detector 4 is divided into detector modules 8. Each detector module 8 is arranged like a flat panel or an arc having the X-ray focus 9 as its corresponding center.

Figure 2:
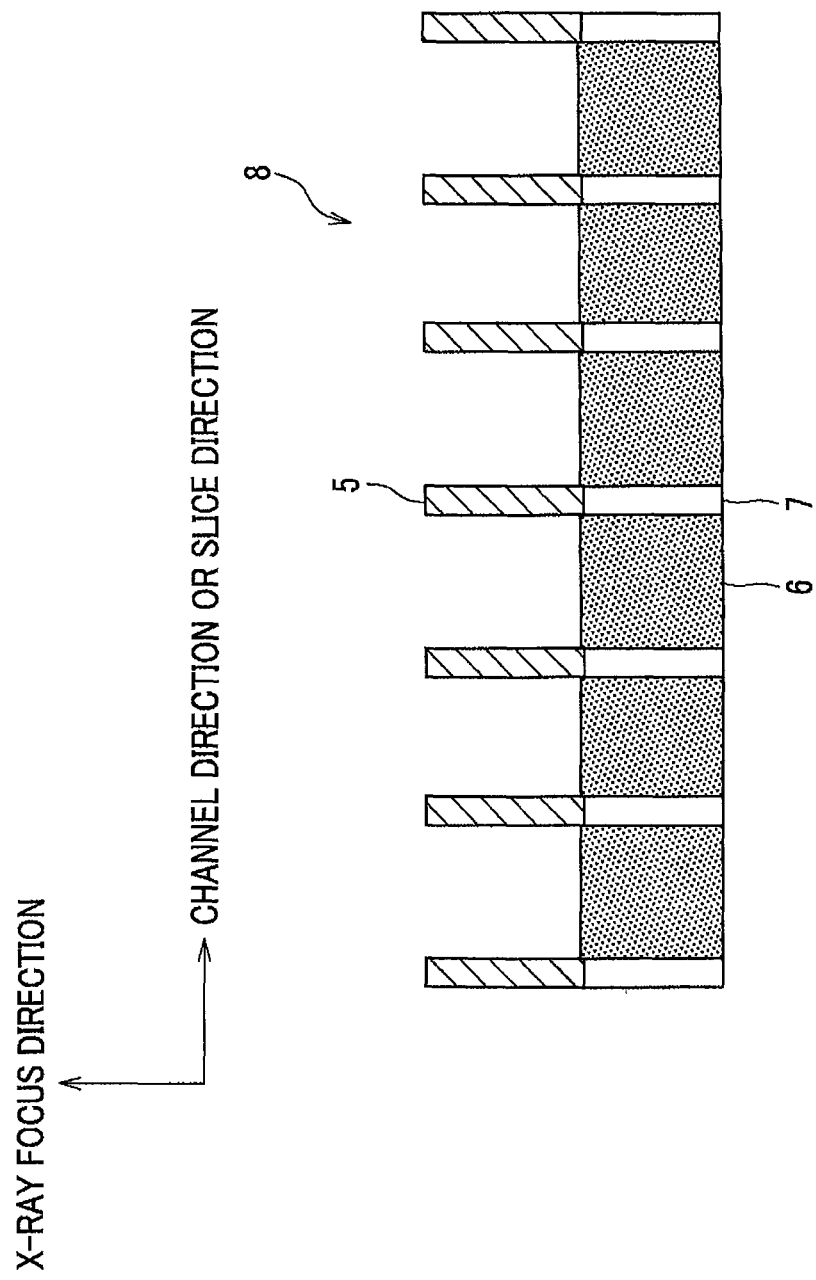
FIG. 2 illustrates the structure of detector modules.

FIG. 2 illustrates the structure of detector modules 8. In the detector modules 8, X-ray detection elements 6 are separated by separators 7 and two-dimensionally disposed in a channel direction (a scanner rotation direction) and a slice direction (a body axial direction). This is because one X-ray radiation is used to obtain X-ray transmission image data (projection data) on a large area of the object 3. Here, examples of the X-ray detection element 6 include a combination of a scintillator and a photodiode and a semiconductor that converts radiation into an electric signal. The X-ray detection element 6 measures X-ray incident intensity on the element. An anti-scatter grid 5 is disposed at the X-ray tube 1 side of the detector modules 8 so as to remove scattered X-rays generated in the object 3, etc.

Now, back to the description of FIG. 1. Based on scan conditions set using an input unit 104 by a user, a control unit 103 uses a storage unit 101 and a calculation unit 102 to control a scan of the X-ray CT scanner 100. The storage unit 101 stores a large number of projection data obtained by rotation scanning. Next, the calculation unit 102 executes image processing. Then, an output unit 105 displays the post-image-processing projection data as information such as a tomographic image of the object 3.

<Image Creation Processing of X-ray CT Scanner 100>
The following describes image creation processing of the X-ray CT scanner 100. The projection data (X-ray transmission image data) scanned by the X-ray CT scanner 100 include scattered X-rays generated in the object 3. Because of this, the X-ray CT scanner 100 performs general image correction processing as well as estimates a point spread function (PSF) having considered a distribution of the scattered X-rays generated in the object 3, which distribution varies depending on each scanning. Then, correction is made to create an image.

Figure 3:
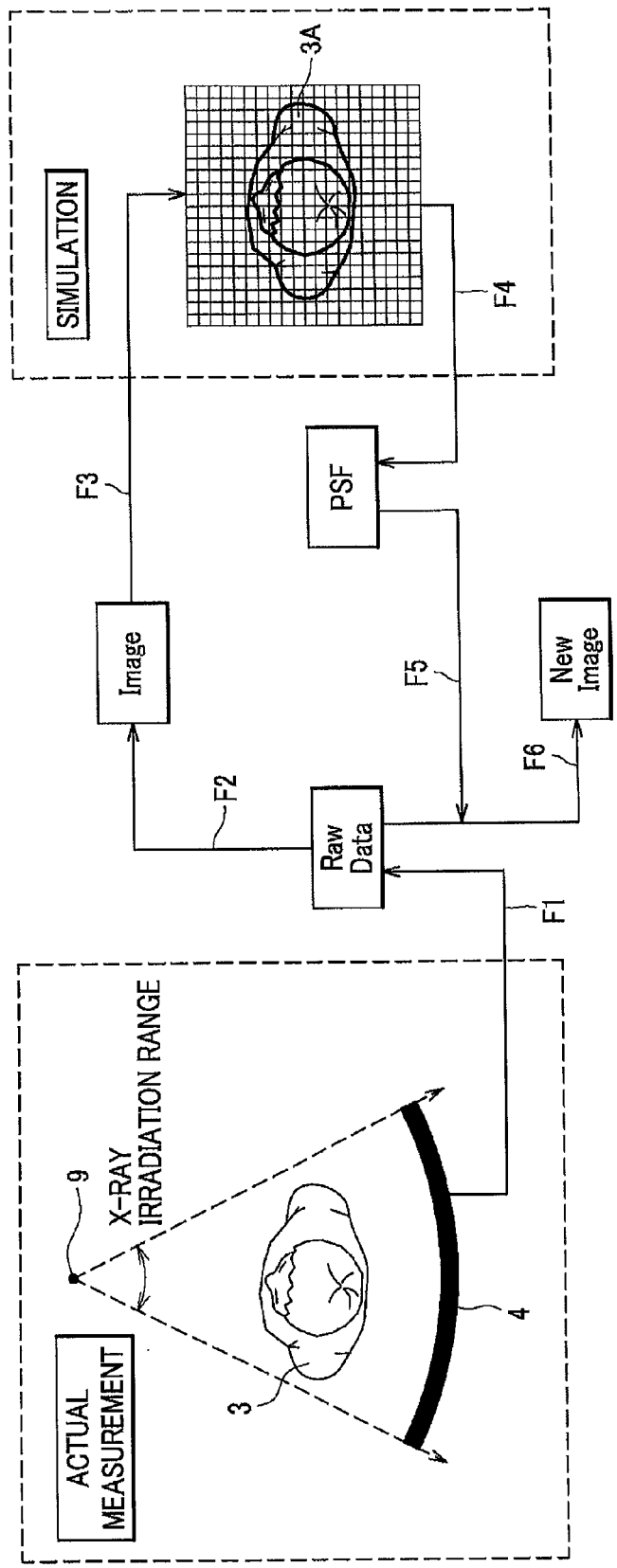
FIG. 3 outlines image creation processing of an X-ray CT scanner according to the first embodiment.

FIG. 3 outlines image creation processing of the X-ray CT scanner.

The X-ray CT scanner 100 performs correction and reconstruction processing (F2) on the projection data (Raw Data) as obtained by the scanning (F1) to create a reconstruction image (Image). Note that the correction and reconstruction processing in the step F2 refers to general image correction processing such as sensitivity correction.

Subsequently, the calculation unit 102 of the X-ray CT scanner 100 simulates (F3) the object 3 on the calculation unit 102 (see FIG. 1) based on the reconstruction image (Image) as produced by the correction and reconstruction processing (F2). Then, a simulation object 3A as simulated in F3 is subjected to a Monte Carlo simulation (F4) that can calculate a detailed X-ray physical interaction. This makes it possible to precisely estimate a point spread function (PSF) that reflects the structure of the object 3, which function varies depending on each scanning. Note that the reconstruction image (Image) before scatter correction may have artifacts due to the scattered X-rays. Unless the artifacts severely affect the image, it is possible to read information on the internal structure of the object 3 from the reconstruction image.

Based on the point spread function (PSF) as estimated in F4, the calculation unit 102 corrects (F5) the projection data (Raw Data) as obtained by the scanning (F1). Specifically, scattered X-ray components are removed from the projection data. After that, the calculation unit 102 subjects the projection data after removal of the scattered X-ray components to additional correction and reconstruction processing (F6). This makes it possible for the calculation unit 102 to obtain a superior reconstruction image (New Image) having a less scattered X-ray effect than the reconstruction image (Image) as produced in the correction and reconstruction processing (F2). Note that the correction and reconstruction processing in the step F6 refers to general image correction processing such as sensitivity correction in the same manner as in F2.

<Detailed Image Creation Processing>

The following details each step of the image creation processing as shown in FIG. 3.

Note that the scanning (F1), the correction and reconstruction processing (F2), and the correction and reconstruction processing (F6) are general scanning and image correction processing of the X-ray CT scanner 100, so that their descriptions are omitted.

(Simulation of Object 3: F3)

During F3 in FIG. 3, the calculation unit 102 of the X-ray CT scanner 100 simulates the object 3 based on the reconstruction image (Image) by using a calculator to produce a simulation object 3A. Here, the reconstruction image (Image) is represented by CT numbers that reflect differences in an X-ray absorption coefficient inside the object 3. For the CT numbers, water is assigned to 0 HU and air is assigned to −1000 HU. Although a Monte Carlo simulation requires an element composition and density of substances, the composition and density cannot be determined from only the CT numbers.

Accordingly, in the X-ray CT scanner 100, some of the substances whose composition, density, and CT number are known are predefined as substances constituting the object 3. Next, substances having an intermediate CT number are assigned to a mixture of the defined substances. Then, the X-ray CT scanner 100 simulates the internal structure (i.e., an X-ray absorption coefficient distribution) of the object 3. Specifically, for each pixel of the reconstruction image, a component substance is defined, for example, as a defined substance or a mixture of the defined substances.

Figure 4A:
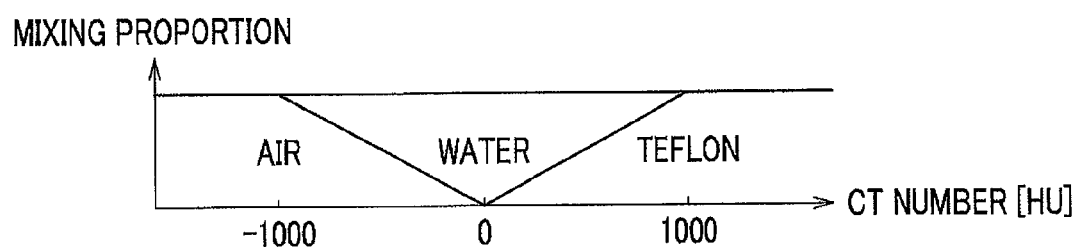
FIG. 4 is an example illustrating how to define substances used to simulate an object.

FIG. 4 is an example illustrating how to define substances used to simulate the object 3. FIG. 4A illustrates that air, water, and Teflon (a registered trademark; the same applies to the following) are assigned as representative substances having a CT number of −1000 HU, 0 HU, and 1000 HU, respectively. A substances having a given CT number is assigned as a mixture of the above defined substances. The following shows their compositions. Note that in FIG. 4, the abscissa represents a CT number and the ordinate represents a proportion of the mixed representative substances.

Air:Water:Teflon=100%:0%:0% (in the case of a CT number≤−1000 HU);

Air:Water:Teflon=A%:(100−A)%:0% (in the case of −1000 HU<a CT number≤0 HU);

Air:Water:Teflon=0%:(100−B)%:B% (in the case of 0 HU<a CT number≤1000 HU); and

Air:Water:Teflon=0%:0%:100% (in the case of 1000 HU<a CT number).

Here, the proportion is a volume ratio. In addition, the "A" and "B" are represented by the following (Equation 1) and (Equation 2), respectively.

$$A=-CT \text{ number}[HU]/1000 \times 100 \quad \text{(Equation 1)}$$

$$B=CT \text{ number}[HU]/1000 \times 100 \quad \text{(Equation 2)}$$

Note that the composition of the object 3 may be somehow estimated. In this case, abundant substances in the object 3 are selected as representative substances. Then, rare substances in the object 3 are not selected as the representative substances. This operation allows for high precision and accuracy. In this regard, however, because any CT number may be interpolated, the representative substances should have a broad range of the CT number.

Figure 4B:
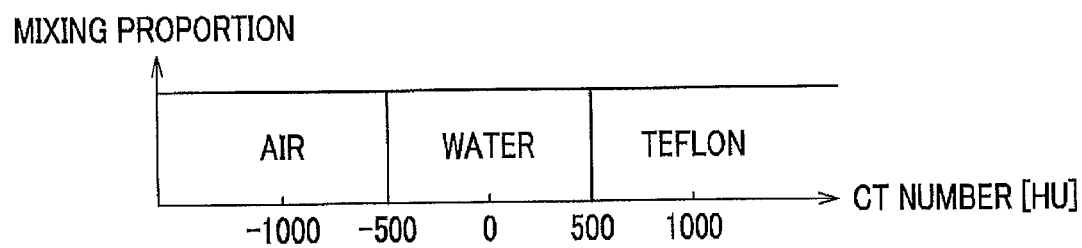

In addition, in order to reduce a calculation load, a single substance is used to replace a region within a certain range of the CT number. For example, FIG. 4B illustrates the following possible setting.

Air (in the case of a CT number≤−500 HU);

Water (in the case of −500 HU<a CT number≤500 HU); and

Teflon (in the case of 500 HU<a CT number).

The following describes a simulation of the shape of the object 3. A reconstruction image (Image) is represented by, for example, a matrix having 512×512 pixels. By reflecting the above, 512×512 voxels per slice are used to represent the object 3 on the calculation unit 102. Then, the above-defined component substance information is assigned to each voxel. That is, the simulation object 3A is formed of an assembly of rectangular parallelepiped regions including surrounding air.

Note that except for the case of scanning the whole object 3, the region scanned by the X-ray CT scanner 100 is limited to some portions of the object 3. In that case, information outside the reconstruction region of the object 3 may not be obtained, but scattered X-rays may interact with the outside of the reconstruction region to reenter the reconstruction region. Because of this, it is required to simulate the structure of the outside of the reconstruction region of the object 3. In this case, for example, it is possible to adopt a method for defining the structure indicated by pixels surrounding the reconstruction region as a uniform structure outside a visualized field.

(Execution of Monte Carlo Simulation on Simulation Object 3A: F4)

The following describes a Monte Carlo simulation (F4 in FIG. 3) on a simulation object 3A that is simulated on the calculation unit 102. The calculation unit 102 of the X-ray CT scanner 100 uses the Monte Carlo simulation to obtain projection data when an X-ray projection is carried out on the object 3 reconstituted on the calculation unit 102 in the same manner as in the actual scanning. At this occasion, conditions other than those of the object 3, including the device structures such as an X-ray source (e.g., an X-ray tube 1, an X-ray focus 9) and an X-ray detector 4, are also simulated on the calculation unit 102 in substantially the same manner as in the actual structures.

The X-ray CT scanner 100 uses the Monte Carlo simulation to irradiate the simulation object 3 with a pencil X-ray beam, and then estimates an X-ray intensity distribution (i.e., a point spread function p) on the surface of the X-ray detector 4 with respect to an X-ray incident direction. The results are set as the measured projection data g(ch, sl), scattered-X-ray-free ideal projection data t(ch, sl), and point spread function p(ch, sl). These data are converted using a Fourier transformation to G(CH, SL), T(CH, SL), and P(CH, SL). Then, the following (Equation 3) and (Equation 4) are known to hold. Here, the "CH" and "SL" represent frequency components of a ch direction and a sl direction, respectively.

$$g=t*p \quad \text{(Equation 3); and}$$

$$G=T \cdot P \quad \text{(Equation 4),}$$

wherein the "*" denotes a convolution integral and the "·" denotes a product. Note that variable representation is omitted.

When F denotes an inverse Fourier transformation, the ideal projection data t of interest is given in the following (Equation 5):

$$t=F[G/P]=g*F[1/P] \quad \text{(Equation 5).}$$

This method is called a deconvolution integral method.

How the scattered X-rays spread varies depending on a region of the object 3 and a scan angle direction θ'. The (ch', sl') may be assigned to the position of the detector element 6 that is disposed in an incident direction of a pencil beam. In this case, the point spread function p that depends on the X-ray incident direction is represented by the following (Equation 6):

$$p(ch, sl, ch', sl', \theta') \quad \text{(Equation 6).}$$

In the X-ray CT scanner 100, the point spread function is presumed to change relatively gradually. In order to make calculation faster, the point spread function is calculated only for some of the representative projection angles and detector element 6 positions (ch', sl', θ'). For examples, the X-ray detector 4 is divided into 10 regions in a channel direction. Then, the point spread function is calculated for the detector element 6 position (ch', sl') which is situated in the center of each region. The calculated point spread function and (Equation 5) are used to yield ideal projection data t of each region (F5).

In addition, the point spread functions p regarding the representative projection angles and positions can be used to estimate and interpolate point spread functions regarding intermediate projection angles and positions. In this case, the point spread function p is assumed as, for example, a function of a distance (|ch|) from the representative position. The function is subjected to fitting using C·EXP(−D·|ch|) to calculate coefficients C and D. These coefficients are used to carry out data interpolation. Here, the "EXP" denotes an exponential function.

Note that the Monte Carlo simulation may use insufficient statistics, which produces high frequency components. In order to remove the high frequency components, the point spread function distribution or the fitting parameter distribution may be subjected to smoothing processing. The smoothing processing is carried out using a data moving average in a channel, slice, or projection angle direction. By using such a procedure, the X-ray CT scanner 100 may calculate ideal projection data t in all the projection angle directions to renew the image. The above can create a high-quality image without being affected by the scattered X-rays.

As described above, the X-ray CT scanner 100 according to the first embodiment uses the reconstruction image of the object 3 to estimate a point spread function of a scatter derived from the object 3. This can reproduce a change in the structure corresponding to the object 3. The above makes it possible for the X-ray CT scanner 100 to precisely estimate the point spread function. In addition, the above can decrease occurrence of poor image quality due to the scattered X-rays. Further, the X-ray CT scanner 100 according to the first embodiment uses a Monte Carlo simulation that can strictly simulate a physical interaction, so that the point spread function can be precisely estimated.

Furthermore, in the X-ray CT scanner 100 according to the first embodiment, the projection angles are limited to representative angle directions and the positions of the X-ray detection elements 6 are limited to representative positions. Then, a simulation is executed to calculate a point spread function. Also, point spread functions on other projection angles and X-ray detection element 6 positions are calculated using interpolation. Thus, the above can markedly shorten a calculation time required for the scatter correction. Moreover, in the X-ray CT scanner 100 according to the first embodiment, the point spread function distribution and its fitting parameter distribution as obtained by the calculation are subjected to smoothing processing. This processing may be used to remove high frequency noise due to a statistical fluctuation, which enables the calculation time to be shortened and excessive and improper correction to be reduced. That is, the X-ray CT scanner 100 according to the first embodiment can produce a high-quality CT image within a practical calculation time without being affected by scattered X-rays.

<<Second Embodiment>>

In the first embodiment, point spread functions on representative points have been estimated to carry out scatter correction. In the second embodiment, a scattered X-ray distribution has been estimated using a Monte Carlo simulation to carry out scatter correction. Note that in the second embodiment, how to construct an X-ray CT scanner 100 (see FIGS. 1 and 2) is substantially the same as in the first embodiment, so that the detailed description is omitted.

<Image Creation Processing of X-ray CT Scanner 100>

The following describes image creation processing of an X-ray CT scanner 100 according to the second embodiment. The projection data (X-ray transmission image data) scanned by the X-ray CT scanner 100 include scattered X-rays generated in the object 3. Because of this, the X-ray CT scanner 100 performs general image correction processing as well as estimates a distribution of the scattered X-rays generated in the object 3, which distribution varies depending on each scanning. Then, correction is made to create an image.

Figure 5:
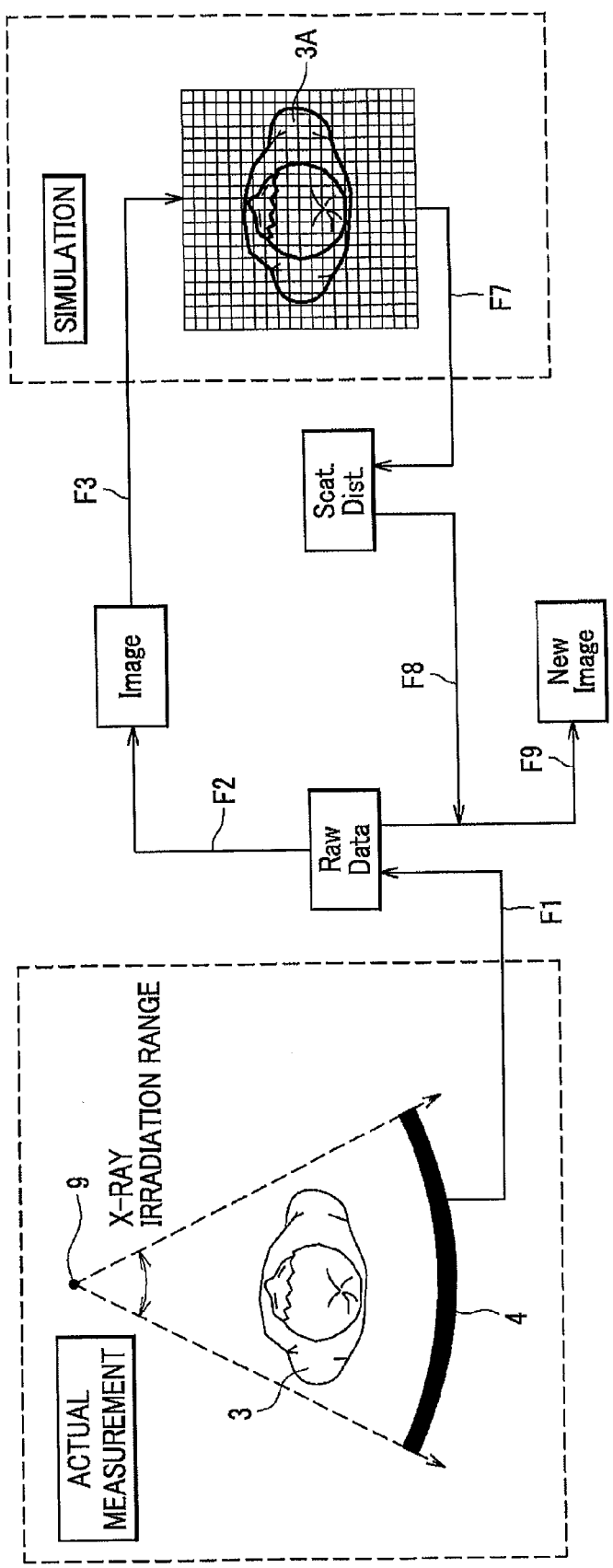
FIG. 5 outlines image creation processing of an X-ray CT scanner according to the second embodiment.

FIG. 5 outlines image creation processing of the X-ray CT scanner according to the second embodiment.

The same image creation processing as of the X-ray CT scanner 100 according to the first embodiment applies to scanning (F1), correction and reconstruction processing (F2), and a simulation of an object 3 (F3), so that their descriptions are omitted.

Then, a simulation object 3A as simulated in F3 is subjected to a Monte Carlo simulation (F7) that can calculate a detailed X-ray physical interaction. This makes it possible to precisely estimate a scattered X-ray distribution (Scat.Dist.) that reflects the structure of the object 3, which distribution varies depending on each scanning. Note that the reconstruction image (Image) before scatter correction may have artifacts due to the scattered X-rays. Unless the artifacts severely affect the image, it is possible to read information on the internal structure of the object 3 from the reconstruction image.

Based on the scattered X-ray distribution as estimated in F7, the calculation unit 102 corrects (F8) the projection data (Raw Data) as obtained by the scanning (F1). Specifically, scattered X-ray components are removed from the projection data. After that, the calculation unit 102 subjects the projection data after removal of the scattered X-ray components to additional correction and reconstruction processing (F9). This makes it possible for the calculation unit 102 to obtain a superior reconstruction image (New Image) having a less scattered X-ray effect than the reconstruction image (Image) as produced in the correction and reconstruction processing (F2). Note that the correction and reconstruction processing in the step F9 refers to general image correction processing such as sensitivity correction in the same manner as in F2.

<Detailed Image Creation Processing>

The following details each step of the image creation processing as shown in FIG. 5.

Note that the scanning (F1), the correction and reconstruction processing (F2), and the correction and reconstruction processing (F9) are general scanning and image correction processing of the X-ray CT scanner 100, so that their descriptions are omitted. The simulation of the object 3 (F3) is the same as in the first embodiment, so that its description is skipped.

(Execution of Monte Carlo Simulation on Simulation Object 3A: F7)

The following describes a Monte Carlo simulation (F7 in FIG. 5) on a simulation object 3A that is simulated on the calculation unit 102. The calculation unit 102 of the X-ray CT scanner 100 uses the Monte Carlo simulation to obtain projection data when an X-ray projection is carried out on the object 3 reconstituted on the calculation unit 102 in the same manner as in the actual scanning. At this occasion, conditions other than those of the object 3, including the device structures such as an X-ray source (e.g., an X-ray tube 1, an X-ray focus 9) and an X-ray detector 4, are also simulated on the calculation unit 102 in substantially the same manner as in the actual structures.

In the Monte Carlo simulation, the X-ray focus 9 emits X-rays as a number of photons. X-ray energy is distributed to each photon based on an energy spectrum under each predetermined scanning condition. A probability is used to describe an interaction given to each photon. Whether or not the interaction is present is determined using a pseudo-random number. Examples of an X-ray-related representative physical process include Compton scattering, Rayleigh scattering, a photoelectric effect, and characteristic X-ray radiation.

The same as in the actual scanning applies to the Monte Carlo simulation. That is, the scanning is performed on a simulation space from a plurality of angle directions while an X-ray source (i.e., an X-ray tube 1 and an X-ray focus 9) and an X-ray detector 4 rotate around an object 3. Then, projection data are calculated. At this occasion, the Monte Carlo simulation can provide information on whether or not there is an interaction between X-rays and the object 3. Accordingly, the simulation can individually calculate each of the incident intensity of primary X-rays and the incident intensity of scattered X-rays detected on the X-ray detector 4.

In this way, the Monte Carlo simulation is executed on the simulation object 3A. By doing so, it is possible to precisely estimate a scattered X-ray distribution (Scat.Dist.) in which the object 3 is considered.

The following describe how to make calculation faster in the Monte Carlo simulation. In an actual CT scanning, depending on scanning conditions, projection data for about 1000 slices per rotation are used to reconstitute an image. That is, in the actual scanning, an object is scanned from different angles about 1000 times per rotation.

Meanwhile, in a simulation performed by the calculation unit 102 of the X-ray CT scanner 100, projection data as obtained only from a less number of representative angle directions than those of the actual scanning are calculated in the simulation. This is because a scattered X-ray distribution has a relatively gradual change compared with a primary X-ray distribution. Accordingly, the scattered X-ray distribution included in the projection data obtained from some of the representative angle directions can be used to estimate scattered X-ray distributions with respect to other angle directions. In this way, a projection simulation is performed only from the representative angle directions. This makes it possible to shorten a calculation time required for the simulation.

The representative angle directions may be selected at random or using an equal angle interval. In order to precisely reproduce the scattered X-ray distributions within a limited calculation time, however, the following setting, for example, may be chosen.

Figure 6:
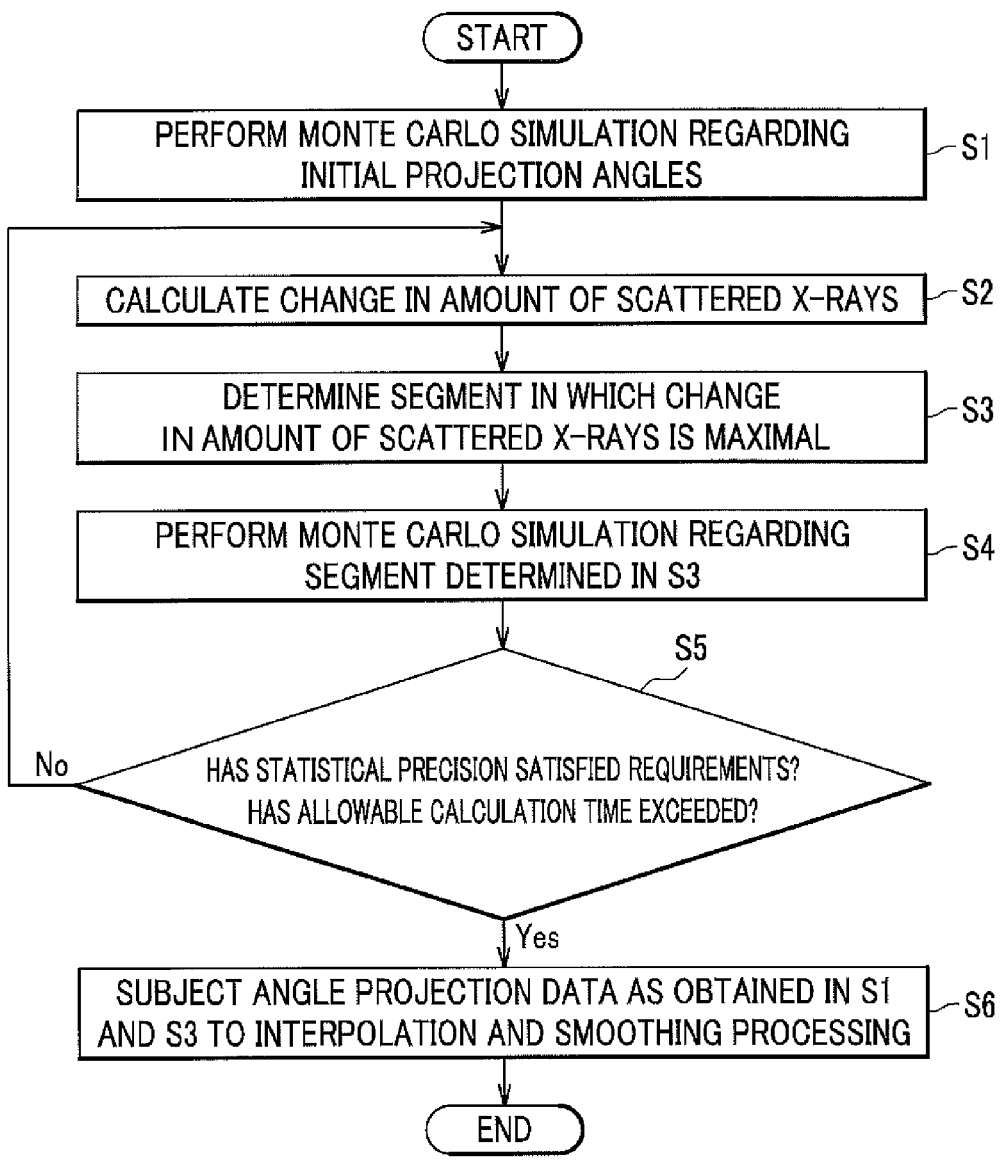
FIG. 6 is a flow chart showing the procedure of a Monte Carlo simulation as an example.

FIG. 6 is a flow chart showing the procedure of a Monte Carlo simulation as an example.

In step S1, the calculation unit 102 performs the above Monte Carlo simulation on predetermined initial projection angles (e.g., 0, 90, 180, and 270 degrees) to calculate a scattered X-ray distribution.

In step S2, the calculation unit 102 calculates a change in an amount of scattered X-rays according to the following (Equation 7).

In the following (Equation 7), data$^{scat}$(ch, sl, θ) represents a scattered X-ray distribution as obtained per rotation of the detector. The distribution is expressed as a function of a position (ch) of the X-ray detection element 6 in a channel direction, a position (sl) of the X-ray detection element 6 in a slice direction, and a projection angle (θ). Note that the "ch", "sl", and "θ" are discrete variables.

[Expression 1]

$$\left| \frac{d}{d\theta} \sum_{ch,sl} data^{scat}(ch, sl, \theta) \right|$$ (Equation 7)

In step S3, the calculation unit 102 determines a segment in which the change in the amount of scattered X-rays is maximal.

In step S4, the calculation unit 102 sets a projection angle to within the segment determined in step S3, and performs the above-mentioned Monte Carlo simulation to calculate a scattered X-ray distribution.

When the above change (Equation 7) is maximal between the projection angles θ1 and θ2 (S3), the calculation unit 102 set the next projection angle to, for example, (θ1+θ2)/2. Then, the Monte Carlo simulation is re-executed to calculate a scattered X-ray distribution (S4).

In step S5, the calculation unit 102 returns to step S2 unless statistical precision requirements have been met or an allowable calculation time has passed (S5: No). Then, the subsequent processes are repeated. If the statistical precision requirements have been met or the allowable calculation time has passed (S5: Yes), the process goes to step S6.

Here, a time required for the Monte Carlo simulation varies depending on the precision requirements. When scatter correction is made, a user can use the input device 104 to optionally set X-ray statistics or a calculation time used for the Monte Carlo simulation. In addition, the user can interrupt the Monte Carlo simulation at any desired timing. When the user interrupts the simulation, the X-ray CT scanner 100 makes the scatter correction by using data for which calculation has been completed by the time of the interruption.

In step S6, the calculation unit 102 subjects the scattered X-ray distributions as obtained in steps S1 and S4 to interpolation processing and smoothing processing to complete the procedure according to this flow chart.

The interpolation processing of step S6 is to interpolate intermediate angle data because the scattered X-ray distribution as obtained in the above processing has a less number of data regarding projection angle directions than those of an actual measurement. Examples of a known data interpolation method include a spline interpolation method and a Lagrange interpolation method. In addition, the smoothing processing of step S6 is to remove high frequency components generated due to insufficient statistics for the Monte Carlo simulation. The smoothing processing is carried out using a data moving average in a channel, slice, or projection angle direction.

(Scatter Correction Using Scatted X-ray Distribution: F8)

The following details scatter correction (F8 in FIG. 5) that corrects, based on the scattered X-ray distribution estimated in F7, projection data (Raw Data) as obtained by the scanning (F1). The calculation unit 102 of the X-ray CT scanner 100 uses the scattered X-ray distribution as obtained by the simulation to subtract the scatted X-ray contribution from the projection data as obtained by the scanning.

Specifically, the calculation unit 102 executes calculation set forth in the following (Equation 8) to make scatter correction. In the following (Equation 8), DATA denotes projection data obtained by scanning; DATA$_{ref}$ denotes projection reference data obtained by the scanning (e.g., average output data of an X-ray detection element 6 positioned at an edge portion); data$^{scat}$ denotes scattered X-ray distribution data obtained by calculation; and data$^{total}_{ref}$ denotes reference data of the total X-ray distribution (=a primary X-ray distribution+a scattered X-ray distribution) obtained by the calculation. Variable representation is omitted. In addition, α is a constant representing correction intensity. Note that measured data are corrected to have an output (i.e., an offset value) of 0 when an object is not irradiated with X-rays.

[Expression 2]

$$NewData = \frac{DATA}{DATA_{ref}} - \alpha \frac{data^{scat}}{data^{total}_{ref}} \quad \text{(Equation 8)}$$

Further, the calculation unit 102 performs calculation according to the following (Equation 9) to make scatter correction on air data (i.e., an output value when the object 3 is assumed as air). In the following (Equation 9), AIR denotes projection data when the object 3 is scanned as air. In addition, each index means the same as in the above (Equation 8).

[Expression 3]

$$NewAir = \frac{AIR}{AIR_{ref}} - \alpha \frac{air^{scat}}{air^{total}_{ref}} \quad \text{(Equation 9)}$$

The calculation unit 102 uses the values calculated using the above (Equation 8) and (Equation 9) to make sensitivity correction (also referred to as air calibration) regarding the X-ray detection element 6 by using the following (Equation 10):

NewData/NewAir  (Equation 10).

The calculation unit 102 uses data after the scatter correction and the air calibration as described in the above (Equation 10) to reconstruct an image one more time. This makes it possible for the X-ray CT scanner 100 to provide a user with a high-quality image without being affected by scattered X-rays.

Note that the above describes the case of having the air calibration after the scatter correction, but it is possible to make the scatter correction after the air calibration. In this regard, however, the scattered X-rays included in the air data are not taken into consideration because the scattered X-ray contribution is small. Specifically, calculation is carried out according to the following (Equation 11).

[Expression 4]

$$\frac{DATA}{DATA_{ref}} / \frac{AIR}{AIR_{ref}} - \alpha \frac{data^{scat}}{air^{total}} \quad \text{(Equation 11)}$$

As described above, the X-ray CT scanner 100 according to the second embodiment uses a reconstruction image (Image) of the object 3 to estimate a scattered X-ray distribution (Scat.Dist.). This can reproduce a change in the structure corresponding to the object 3. The above makes it possible for the X-ray CT scanner 100 to precisely estimate the scattered X-ray distribution. In addition, the above can decrease occurrence of poor image quality due to the scattered X-rays. Further, the X-ray CT scanner 100 according to the second embodiment uses a Monte Carlo simulation that can strictly simulate a physical interaction, so that the scattered X-ray distribution can be precisely estimated.

Furthermore, in the X-ray CT scanner 100 according to the second embodiment, the projection angles are limited to representative angle directions. Then, a simulation is executed to calculate a scattered X-ray distribution. Scattered X-ray distributions with respect to other angle directions are determined using interpolation. Thus, the above can markedly shorten a calculation time required for estimation of the scattered X-ray distribution. Moreover, in the X-ray CT scanner 100 according to the second embodiment, the scattered X-ray distribution calculated is subjected to smoothing processing. This processing may be used to remove high frequency noise due to a statistical fluctuation, which enables the calculation time to be shortened and excessive and improper correction to be reduced. That is, the X-ray CT scanner 100 according to the second embodiment can produce a high-quality CT image within a practical calculation time without being affected by scattered X-rays.

<<Third Embodiment>>

In the first and second embodiments, whenever a measurement (scanning: F1) is performed on an object 3, a Monte Carlo simulation (F4) is carried out on a simulation object 3A (an X-ray absorption coefficient distribution) to calculate a scattered X-ray distribution and/or a point spread function. In the third embodiment, an object 3 is beforehand simulated to define a phantom (i.e., a simulated object) in which the object 3 is simulated. The methods described in the first and second embodiments are used to calculate in detail a scattered X-ray distribution or a point spread function. This can markedly shorten a time required for scatter correction. Note that in the third embodiment, how to construct an X-ray CT scanner 100 (see FIGS. 1 and 2) and how to process image creation processing (see FIGS. 3 and 5) are substantially the same as in the first and second embodiments, so that the detailed description is omitted.

In the third embodiment, the X-ray CT scanner 100 uses, for example, elliptic cylinder-shaped water as a phantom. This is because an elliptic cylinder has variables of only a major radius a and a minor radius b. Hereinafter, an ellipticity (f=1−b/a) is a variable used as a substitute for the minor radius b. Before the object 3 is actually measured, the X-ray CT scanner 100 calculate how a scattered X-ray distribution or a point spread function depends on the major axis a of each of elliptic cylinders having different ellipticities f. Then, the X-ray CT scanner 100 calculates a scattered X-ray distribution and/or a point spread function distribution for the given variables a and f by interpolation and/or function fitting to store the results in a database.

When an object 3 is actually scanned, the X-ray CT scanner 100 uses a reconstruction image obtained by the scanning to fit the shape of the scanning region of the object 3 to an ellipse. Next, a major radius a and an ellipticity f of the ellipse are determined. Then, the X-ray CT scanner 100 uses the determined major radius a and the ellipticity f to select a corresponding scattered X-ray distribution or point spread function distribution from the above database. After that, the methods described in the first and second embodiments are used to make scatter correction on the measured data. Finally, the X-ray CT scanner 100 uses the post-scatter-correction measurement data to reconstruct an image. The above can create a high-quality image without being affected by the scattered X-rays.

As described above, the X-ray CT scanner 100 according to the third embodiment exerts substantially the same effects as of the X-ray CT scanner 100 according to the first and second embodiments as well as the following additional effect. Specifically, the X-ray CT scanner 100 according to the third embodiment performs a Monte Carlo simulation that requires a long calculation time before the scanning of the object 3, so that a time required for scatter correction can be markedly shortened.

REFERENCE SIGNS LIST

1 X-ray tube (X-ray source)
2 Aperture
3 Object
3A Simulation object (Simulated object, X-ray absorption coefficient distribution)
4 X-ray detector
5 Anti-scatter grid
6 Separator
7 X-ray detection element
8 Detector modules
9 X-ray focus
100 X-ray CT scanner
101 Storage unit
102 Calculation unit
103 Control Unit
104 Input unit
105 Output unit
F1 Scanning (Scanning section)
F2 Correction and reconstruction processing
F3 Simulation of an object (Internal-distribution-estimating section)
F4 Monte Carlo simulation on a simulation object (Point-spread-function-estimating section)
F5 Projection data correction (Correction section)
F6 Correction and reconstruction processing (Image-creating section)
F7 Monte Carlo simulation on a simulation object (X-ray-distribution-estimating section)
F8 Projection data correction (Correction section)
F9 Correction and reconstruction processing (Image-creating section)

The invention claimed is:

1. An X-ray CT scanner comprising:
   a scanning section that scans an object to obtain X-ray transmission image data of the object from a plurality of projection directions, the scanning section comprising an X-ray source generating X-rays from an X-ray focus and an X-ray detector having X-ray detection elements in a two-dimensional array so as to detect the X-rays, wherein the X-ray source and the X-ray detector rotate around the object while facing each other and the object is interposed therebetween;
   an internal-distribution-estimating section that estimates an X-ray absorption coefficient distribution inside the object, based on the X-ray transmission image data scanned by the scanning section;
   a point-spread-function-estimating section that estimates a point spread function of a scatter derived from the object by performing a Monte Carlo simulation to simulate a physical interaction of the X-rays in a simulated object having the X-ray absorption coefficient distribution estimated by the internal-distribution-estimating section;
   a correction section that corrects the X-ray transmission image data by processing the point spread function estimated by the point-spread-function-estimating section and the X-ray transmission image date according to a deconvolution integral method; and
   an image-creating section that creates an image of the X-ray absorption coefficient distribution of the object by using the X-ray transmission image data corrected by the correction section.

2. The X-ray CT scanner according to claim 1, wherein the point-spread-function-estimating section performs the Monte Carlo simulation with respect to representative projection directions, the number of which is less than the number of the plurality of projection directions; the point spread functions obtained by the Monte Carlo simulation are used for interpolation between the representative projection directions to estimate point spread functions regarding all the plurality of projection directions.

3. The X-ray CT scanner according to claim 1, wherein the point-spread-function-estimating section performs the Monte Carlo simulation with respect to representative element positions, the number of which is predetermined in view of the X-ray detection elements in the two-dimensional array; the point spread functions obtained by the Monte Carlo simulation are used for interpolation between the representative element positions to estimate point spread functions regarding all the positions of the X-ray detection elements in the two-dimensional array.

4. The X-ray CT scanner according to claim 1, wherein the internal-distribution-estimating section simulates the object as a mixture of a plurality of substances having a known CT number to estimate the X-ray absorption coefficient distribution.

5. The X-ray CT scanner according to claim 1, further comprising:
   a user interface allowing for at least one operation selected from the group consisting of: a setting of X-ray statistics for the Monte Carlo simulation; a setting of a calculation time for execution of the Monte Carlo simulation; and an interruption at an any desired timing during the Monte Carlo simulation.

6. The X-ray CT scanner according to claim 1, wherein the internal-distribution-estimating section estimates the X-ray absorption coefficient distribution inside the object from an X-ray absorption coefficient distribution of a simulated object that simulates the object instead of estimating, based on the X-ray transmission image data scanned by the scanning section, the X-ray absorption coefficient distribution inside the object.

7. An X-ray CT scanner comprising:
   a scanning section that scans an object to obtain X-ray transmission image data of the object from a plurality of projection directions, the scanning section comprising an X-ray source generating X-rays from an X-ray focus and an X-ray detector having X-ray detection elements in a two-dimensional array so as to detect the X-rays, wherein the X-ray source and the X-ray detector rotate around the object while facing each other and the object is interposed therebetween;
   an internal-distribution-estimating section that estimates an X-ray absorption coefficient distribution inside the object, based on the X-ray transmission image data scanned by the scanning section;
   an X-ray-distribution-estimating section that estimates a distribution of scattered X rays derived from the object by performing a Monte Carlo simulation to simulate a physical interaction of the X-rays in a simulated object having the X-ray absorption coefficient distribution estimated by the internal-distribution-estimating section;

a correction section that removes components of the scattered X-rays from the X-ray transmission image data, based on the distribution estimated by the X-ray-distribution-estimating section; and an image-creating section that creates an image of the X-ray absorption coefficient distribution of the object by using the X-ray transmission image data in which the components of the scattered X-rays have been removed by the correction section.

8. The X-ray CT scanner according to claim 7, wherein the X-ray-distribution-estimating section performs the Monte Carlo simulation with respect to representative projection directions, the number of which is less than the number of the plurality of projection directions; the distributions obtained by the Monte Carlo simulation are used for interpolation between the representative projection directions to estimate distributions regarding all the plurality of projection directions.

9. The X-ray CT scanner according to claim 8, wherein the X-ray-distribution-estimating section estimates a projection direction having a maximal change in an amount of the scattered X-rays from the distributions of the representative projection directions and repeats a process for determining a scattered X-ray distribution of the projection direction having the maximal change by performing the Monte Carlo simulation; and all the representative projection directions are sequentially selected.

10. A method for scatter correction, comprising:

a scanning step of scanning an object to obtain X-ray transmission image data of the object from a plurality of projection directions, a scanning section including an X-ray source generating X-rays from an X-ray focus and an X-ray detector having X-ray detection elements in a two-dimensional array so as to detect the X-rays, wherein the X-ray source and the X-ray detector rotate around the object while facing each other and the object is interposed therebetween;

an internal-distribution-estimating step of estimating an X-ray absorption coefficient distribution inside the object, based on the X-ray transmission image data scanned in the scanning step;

a point-spread-function-estimating step of estimating a point spread function of a scatter derived from the object by performing a Monte Carlo simulation to simulate a physical interaction of the X-rays in a simulated object having the X-ray absorption coefficient distribution estimated in the internal-distribution-estimating step;

a correction step of correcting the X-ray transmission image data by processing the point spread function estimated in the point-spread-function-estimating step and the X-ray transmission image date according to a deconvolution integral method; and an image-creating step of creating an image of the X-ray absorption coefficient distribution of the object by using the X-ray transmission image data corrected in the correction step.

11. A method for scatter correction, comprising:

a scanning step of scanning an object to obtain X-ray transmission image data of the object from a plurality of projection directions, a scanning section including an X-ray source generating X-rays from an X-ray focus and an X-ray detector having X-ray detection elements in a two-dimensional array so as to detect the X-rays, wherein the X-ray source and the X-ray detector rotate around the object while facing each other and the object is interposed therebetween;

an internal-distribution-estimating step of estimating an X-ray absorption coefficient distribution inside the object, based on the X-ray transmission image data scanned in the scanning step;

an X-ray-distribution-estimating step of estimating a distribution of scattered X rays derived from the object by performing a Monte Carlo simulation to simulate a physical interaction of the X-rays in a simulated object having the X-ray absorption coefficient distribution estimated in the internal-distribution-estimating step;

a correction step of removing components of the scattered X-rays from the X-ray transmission image data, based on the distribution estimated in the X-ray-distribution-estimating step; and an image-creating step of creating an image of the X-ray absorption coefficient distribution of the object by using the X-ray transmission image data in which the components of the scattered X-rays have been removed in the correction step.

* * * * *